US009452283B2

United States Patent
Jackson et al.

(10) Patent No.: US 9,452,283 B2
(45) Date of Patent: *Sep. 27, 2016

(54) CUFF ELECTRODE WITH INTEGRATED TENDRIL

(71) Applicant: Cardiac Pacemakers, Inc., St. Paul, MN (US)

(72) Inventors: Timothy R. Jackson, Minneapolis, MN (US); Brian Soltis, St. Paul, MN (US); Kyle True, Minneapolis, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/084,339

(22) Filed: Mar. 29, 2016

(65) Prior Publication Data

US 2016/0206874 A1  Jul. 21, 2016

Related U.S. Application Data

(63) Continuation of application No. 14/176,658, filed on Feb. 10, 2014, now Pat. No. 9,320,889.

(60) Provisional application No. 61/764,306, filed on Feb. 13, 2013.

(51) Int. Cl.
*A61N 1/00* (2006.01)
*A61N 1/05* (2006.01)

(52) U.S. Cl.
CPC ........... *A61N 1/0556* (2013.01); *A61N 1/0558* (2013.01)

(58) Field of Classification Search
CPC .................................................. A61N 1/0556

USPC ..................................... 607/2, 118, 122, 125
See application file for complete search history.

(56) References Cited

U.S. PATENT DOCUMENTS

| 4,177,818 A | 12/1979 | De Pedro |
| 4,573,481 A | 3/1986 | Bullara |
| 4,590,946 A | 5/1986 | Loeb |
| 4,590,949 A | 5/1986 | Pohndorf |
| 4,602,624 A | 7/1986 | Naples et al. |

(Continued)

FOREIGN PATENT DOCUMENTS

| AU | 2012275666 B2 | 6/2015 |
| CN | 102573986 A | 7/2012 |

(Continued)

OTHER PUBLICATIONS

International Preliminary Examination Report, Chapter II, issued in PCT/US2013/029306, completed Aug. 19, 2014, 16 pages.

(Continued)

*Primary Examiner* — Edward Moran
*Assistant Examiner* — Nadia A Mahmood
(74) *Attorney, Agent, or Firm* — Faegre Baker Daniels LLP

(57) ABSTRACT

A neurostimulation lead includes a lead body having a proximal portion and a distal portion and a first conductor extending through the lead body. An electrode cuff can be secured relative to the distal portion of the lead body. The electrode cuff includes a cuff body, a first tendril extending from a first region of the cuff body, a second tendril extending from a second region of the cuff body and a first electrode disposed on the cuff body and electrically connected to the first conductor.

20 Claims, 10 Drawing Sheets

(56) References Cited

U.S. PATENT DOCUMENTS

| | | |
|---|---|---|
| 4,628,942 A | 12/1986 | Sweeney et al. |
| 4,740,170 A | 4/1988 | Lee et al. |
| 4,920,979 A | 5/1990 | Bullara |
| 4,940,065 A | 7/1990 | Tanagho et al. |
| 4,979,511 A | 12/1990 | Terry, Jr. |
| 5,031,621 A | 7/1991 | Grandjean et al. |
| 5,095,905 A | 3/1992 | Klepinski |
| 5,215,089 A | 6/1993 | Baker, Jr. |
| 5,218,089 A | 6/1993 | Mariotti et al. |
| 5,251,634 A | 10/1993 | Weinberg |
| 5,259,394 A | 11/1993 | Bens |
| 5,282,468 A | 2/1994 | Klepinski |
| 5,324,322 A | 6/1994 | Grill, Jr. et al. |
| 5,334,438 A | 8/1994 | Saugnac |
| 5,344,438 A | 9/1994 | Testerman et al. |
| 5,351,394 A | 10/1994 | Weinberg |
| 5,358,516 A | 10/1994 | Myers et al. |
| 5,375,594 A | 12/1994 | Cueva |
| 5,505,201 A | 4/1996 | Grill et al. |
| 5,531,778 A | 7/1996 | Maschino et al. |
| 5,674,272 A | 10/1997 | Bush et al. |
| 5,689,877 A | 11/1997 | Grill et al. |
| 5,755,766 A | 5/1998 | Chastain et al. |
| 5,782,892 A | 7/1998 | Castle et al. |
| 5,871,530 A | 2/1999 | Williams et al. |
| 5,913,876 A | 6/1999 | Taylor et al. |
| 5,964,702 A | 10/1999 | Grill et al. |
| 6,038,479 A | 3/2000 | Werner et al. |
| 6,051,017 A | 4/2000 | Loeb et al. |
| 6,093,197 A | 7/2000 | Bakula et al. |
| 6,174,329 B1 | 1/2001 | Callol et al. |
| 6,178,349 B1 | 1/2001 | Kieval |
| 6,249,708 B1 | 6/2001 | Nelson et al. |
| 6,292,703 B1 | 9/2001 | Meier et al. |
| 6,296,659 B1 | 10/2001 | Foerster |
| 6,308,104 B1 | 10/2001 | Taylor et al. |
| 6,308,105 B1 | 10/2001 | Duysens et al. |
| 6,313,233 B1 | 11/2001 | Kurosawa et al. |
| 6,381,499 B1 | 4/2002 | Taylor et al. |
| 6,423,080 B1 | 7/2002 | Gellman et al. |
| 6,600,956 B2 | 7/2003 | Maschino et al. |
| 6,725,096 B2 | 4/2004 | Chinn et al. |
| 7,047,081 B2 | 5/2006 | Kuzma |
| 7,054,692 B1 | 5/2006 | Whitehurst et al. |
| 7,160,298 B2 | 1/2007 | Lawes et al. |
| 7,212,867 B2 | 5/2007 | Van Venrooij et al. |
| 7,502,650 B2 | 3/2009 | Kieval |
| 7,536,227 B1 | 5/2009 | Poore et al. |
| 7,561,923 B2 | 7/2009 | Libbus et al. |
| 7,711,421 B2 | 5/2010 | Shafer et al. |
| 7,749,273 B2 | 7/2010 | Cauthen, III et al. |
| 7,807,925 B2 | 10/2010 | Zarembo |
| 7,831,311 B2 | 11/2010 | Cross, Jr. et al. |
| 7,891,085 B1 | 2/2011 | Kuzma et al. |
| 7,925,352 B2 | 4/2011 | Stack et al. |
| 7,925,358 B2 | 4/2011 | Belden et al. |
| 7,933,662 B2 | 4/2011 | Marshall et al. |
| 7,957,817 B1 | 6/2011 | Gillespie et al. |
| 7,974,706 B2 | 7/2011 | Moffitt et al. |
| 7,996,092 B2 | 8/2011 | Mrva et al. |
| 8,100,141 B2 | 1/2012 | Slupecki et al. |
| 8,155,757 B1 | 4/2012 | Neisz et al. |
| 8,244,372 B1 | 8/2012 | Zhulati et al. |
| 8,295,948 B2 | 10/2012 | Barker et al. |
| 8,326,418 B2 | 12/2012 | Sommer et al. |
| 8,417,343 B2 | 4/2013 | Bolea et al. |
| 8,452,406 B2 | 5/2013 | Arcot-Krishnamurthy et al. |
| 8,483,845 B2 | 7/2013 | Sage |
| 8,548,593 B2 | 10/2013 | Ternes et al. |
| 8,639,355 B2 | 1/2014 | Soltis |
| 9,114,250 B2 | 8/2015 | True et al. |
| 9,283,379 B2 | 3/2016 | True et al. |
| 9,320,889 B2 | 4/2016 | Jackson et al. |
| 2002/0116042 A1 | 8/2002 | Boling |
| 2002/0128700 A1 | 9/2002 | Cross, Jr. |
| 2003/0040785 A1* | 2/2003 | Maschino ............ A61N 1/0556 607/118 |
| 2003/0236558 A1 | 12/2003 | Whitehurst et al. |
| 2004/0010303 A1 | 1/2004 | Bolea et al. |
| 2004/0111139 A1 | 6/2004 | McCreery |
| 2005/0209655 A1 | 9/2005 | Bradley et al. |
| 2005/0234512 A1 | 10/2005 | Nakao |
| 2005/0283246 A1 | 12/2005 | Cauthen, III et al. |
| 2006/0030919 A1 | 2/2006 | Mrva et al. |
| 2006/0122675 A1 | 6/2006 | Libbus et al. |
| 2006/0190042 A1 | 8/2006 | Stone et al. |
| 2006/0259078 A1 | 11/2006 | Libbus |
| 2007/0071568 A1 | 3/2007 | Dorstewitz |
| 2007/0083236 A1 | 4/2007 | Sikora et al. |
| 2007/0100406 A1 | 5/2007 | Kollatschny et al. |
| 2007/0118177 A1 | 5/2007 | Libbus et al. |
| 2007/0142871 A1 | 6/2007 | Libbus et al. |
| 2007/0173914 A1 | 7/2007 | Kollatschny |
| 2007/0203556 A1 | 8/2007 | Rutten et al. |
| 2007/0239243 A1 | 10/2007 | Moffitt et al. |
| 2007/0255320 A1 | 11/2007 | Inman et al. |
| 2008/0046058 A1 | 2/2008 | Cross et al. |
| 2008/0051839 A1 | 2/2008 | Libbus et al. |
| 2008/0058871 A1 | 3/2008 | Libbus et al. |
| 2008/0058874 A1 | 3/2008 | Westlund et al. |
| 2008/0058901 A1 | 3/2008 | Ternes et al. |
| 2008/0086181 A1 | 4/2008 | Amurthur et al. |
| 2008/0091255 A1 | 4/2008 | Caparso et al. |
| 2008/0103407 A1 | 5/2008 | Bolea et al. |
| 2008/0103545 A1 | 5/2008 | Bolea et al. |
| 2008/0132987 A1 | 6/2008 | Westlund et al. |
| 2008/0140092 A1 | 6/2008 | Stone et al. |
| 2008/0172101 A1 | 7/2008 | Bolea et al. |
| 2008/0177365 A1 | 7/2008 | Bolea et al. |
| 2008/0177366 A1 | 7/2008 | Bolea et al. |
| 2008/0183258 A1 | 7/2008 | Inman |
| 2008/0195188 A1 | 8/2008 | Libbus et al. |
| 2008/0234780 A1 | 9/2008 | Smith et al. |
| 2008/0255613 A1 | 10/2008 | Kaiser et al. |
| 2009/0048641 A1 | 2/2009 | Libbus |
| 2009/0210042 A1 | 8/2009 | Kowalczewski |
| 2009/0259260 A1 | 10/2009 | Bentley et al. |
| 2009/0275997 A1 | 11/2009 | Faltys et al. |
| 2009/0276024 A1 | 11/2009 | Bonde et al. |
| 2009/0318961 A1 | 12/2009 | Stone et al. |
| 2010/0023088 A1 | 1/2010 | Stack et al. |
| 2010/0036451 A1 | 2/2010 | Hoffer |
| 2010/0121405 A1 | 5/2010 | Ternes et al. |
| 2010/0145221 A1 | 6/2010 | Brunnett et al. |
| 2010/0168831 A1 | 7/2010 | Korivi et al. |
| 2010/0211131 A1 | 8/2010 | Williams et al. |
| 2010/0286553 A1 | 11/2010 | Feler et al. |
| 2010/0298916 A1 | 11/2010 | Rabischong et al. |
| 2010/0305674 A1 | 12/2010 | Zarembo et al. |
| 2010/0312320 A1 | 12/2010 | Faltys et al. |
| 2010/0331938 A1 | 12/2010 | Sommer et al. |
| 2011/0004281 A1 | 1/2011 | Jones |
| 2011/0022142 A1 | 1/2011 | Barker et al. |
| 2011/0040257 A1 | 2/2011 | Behymer et al. |
| 2011/0060395 A1 | 3/2011 | Cantlon |
| 2011/0172682 A1 | 7/2011 | Brady et al. |
| 2011/0172701 A1 | 7/2011 | Wales et al. |
| 2012/0022617 A1 | 1/2012 | Tockman et al. |
| 2012/0035691 A1 | 2/2012 | Tockman et al. |
| 2012/0065702 A1 | 3/2012 | Arcot-Krishnamurthy et al. |
| 2012/0158082 A1 | 6/2012 | Katra |
| 2012/0221087 A1 | 8/2012 | Parnis et al. |
| 2013/0005169 A1 | 1/2013 | Soltis et al. |
| 2013/0013045 A1 | 1/2013 | Soltis |
| 2013/0172973 A1 | 7/2013 | Tockman et al. |
| 2013/0253615 A1 | 9/2013 | Arcot-Krishnamurthy et al. |
| 2013/0253624 A1 | 9/2013 | Tockman et al. |
| 2014/0094888 A1 | 4/2014 | True et al. |

FOREIGN PATENT DOCUMENTS

| | | |
|---|---|---|
| EP | 0585553 A1 | 6/1993 |
| EP | 2435129 B1 | 7/2015 |
| EP | 2903685 A1 | 8/2015 |

(56) References Cited

FOREIGN PATENT DOCUMENTS

| | | |
|---|---|---|
| EP | 2903686 A1 | 8/2015 |
| JP | H04503312 A | 6/1992 |
| JP | 2005058456 A | 3/2005 |
| JP | 2008526299 A | 7/2008 |
| JP | 2011152204 A | 8/2011 |
| JP | 2012075670 A | 4/2012 |
| JP | 2012130579 A | 7/2012 |
| JP | 2015511857 A | 4/2015 |
| WO | WO9929366 A1 | 6/1999 |
| WO | WO2004052176 A2 | 6/2004 |
| WO | WO2006093685 A1 | 9/2006 |
| WO | WO2007024164 A1 | 1/2007 |
| WO | WO2008088798 A1 | 7/2008 |
| WO | WO2008094349 A1 | 8/2008 |
| WO | WO2009020639 A1 | 2/2009 |
| WO | WO2009025817 A2 | 2/2009 |
| WO | WO2009100242 A2 | 8/2009 |
| WO | WO2011053766 A1 | 5/2011 |
| WO | 2013142053 A1 | 9/2013 |

OTHER PUBLICATIONS

International Preliminary Report on Patentability issued in PCT/US2013/062560, completed Apr. 7, 2015, 9 pages.
International Preliminary Report on Patentability issued in PCT/US2013/062608, completed Apr. 7, 2015, 8 pages.
International Preliminary Report on Patentability issued in PCT/US2014/015590, mailed Aug. 27, 2015, 10 pages.
International Search Report and Written Opinion Issued in PCT/US2009/063442, mailed Feb. 1, 2010, 11 pages.
International Search Report and Written Opinion Issued in PCT/US2010/026350, mailed Jun. 2, 2010.
International Search Report and Written Opinion issued in PCT/US2011/020699, mailed Jul. 26, 2011, 24 pages.
International Search Report and Written Opinion Issued in PCT/US2011/049585, mailed Dec. 19, 2011.
International Search Report and Written Opinion Issued in PCT/US2012/044020, mailed Sep. 11, 2012, 9 pages.
International Search Report and Written Opinion issued in PCT/US2012/044028, mailed Oct. 1, 2012, 9 pages.
International Search Report and Written Opinion issued in PCT/US2012/071812, mailed Sep. 13, 2013, 12 pages.
International Search Report and Written Opinion issued in PCT/US2013/029306, mailed Jul. 18, 2013, 13 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
International Search Report and Written Opinion issued in PCT/US2013/077949, mailed Jun. 20, 2014, 15 pages.
International Search Report and Written Opinion issued in PCT/US2014/015590, mailed May 28, 2014, 14 pages.
Kirsch, Robert F. et al., "Restoration of Hand and Arm Function by Functional Neuromuscular Stimulation", Period covered: Jun. 1, 2001-Aug. 31, 2006, 71 pages.
Partial International Search Report issued in PCT/US2011/020699, mailed Mar. 24, 2011, 6 pages.
Written Opinion of the International Preliminary Examining Authority issued in PCT/US2013/029306, mailed May 8, 2014, 6 pages.

* cited by examiner

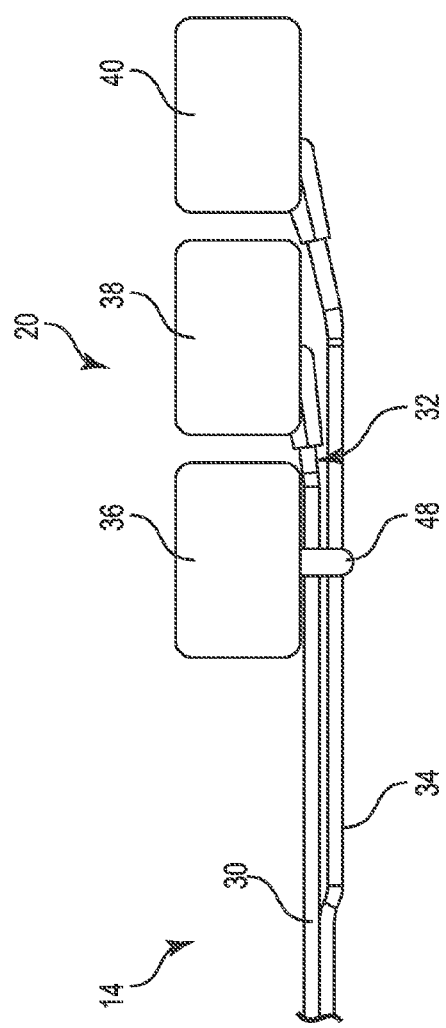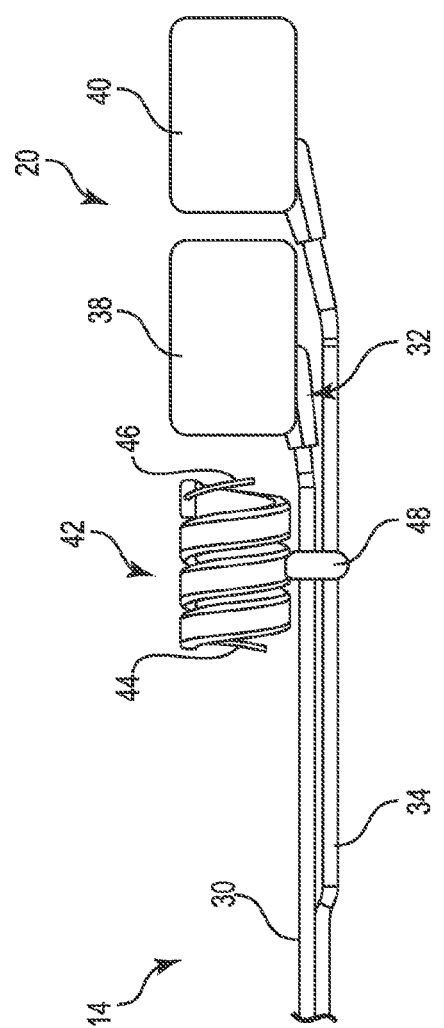

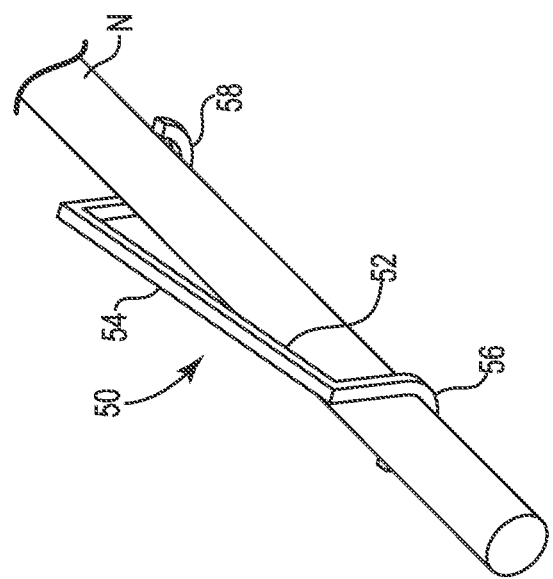
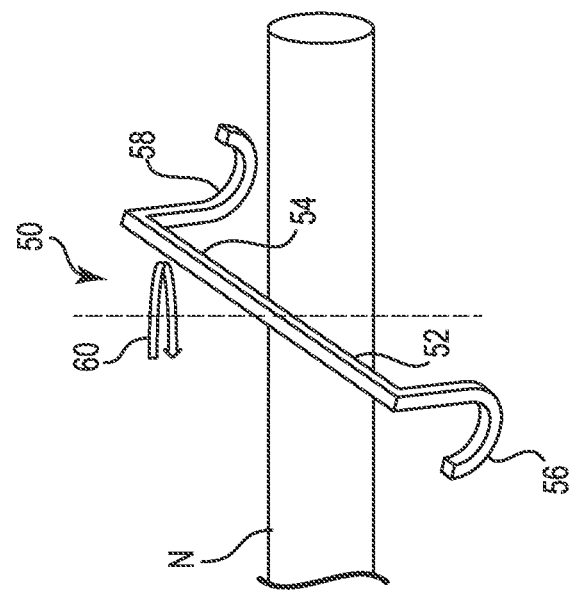

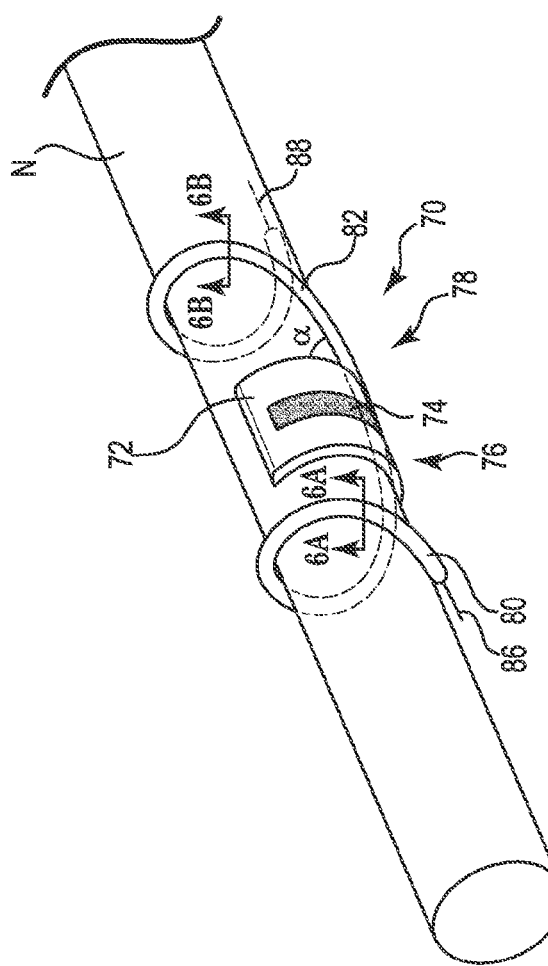
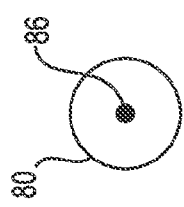
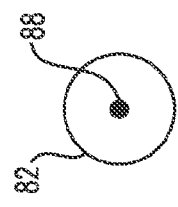

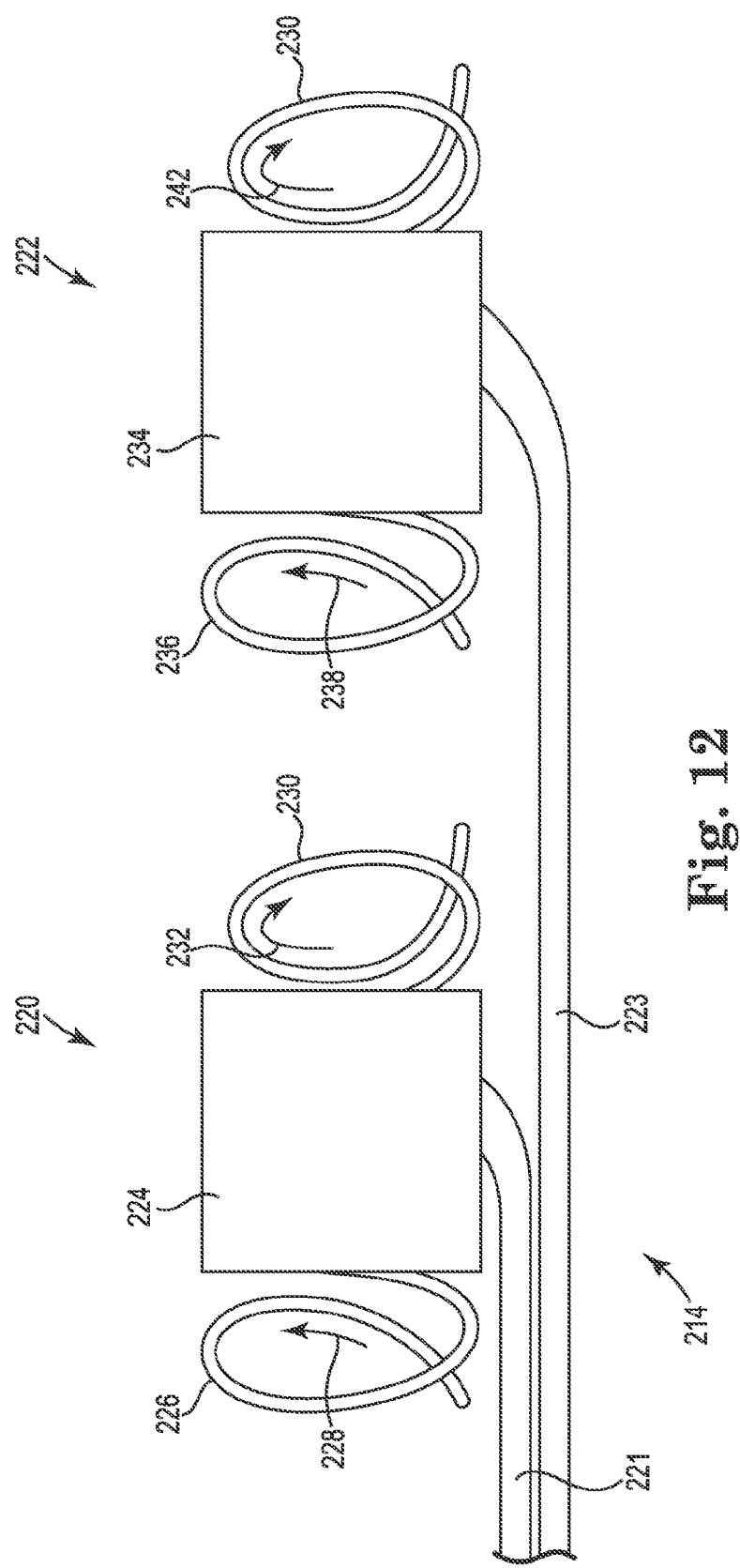

CUFF ELECTRODE WITH INTEGRATED TENDRIL

CROSS-REFERENCE TO RELATED APPLICATIONS

This application is a continuation of U.S. application Ser. No. 14/176,658, filed Feb. 10, 2014, now U.S. Pat. No. 9,320,889, which claims the benefit under 35 U.S.C. section 119(e) to U.S. Provisional Application 61/764,306, filed on Feb. 13, 2013, all of which are herein incorporated by reference in their entirety.

TECHNICAL FIELD

The present invention relates generally to implantable medical devices. More specifically, the present invention relates to medical device leads including helical neurostimulation electrodes

BACKGROUND

A significant amount of research has been directed both to the direct and indirect stimulation and sensing of the left and right vagus nerves, the phrenic nerve, the sacral nerve, the cavernous nerve, and portions of the anatomy with baroreceptors (e.g., the carotid artery) to treat a wide variety of medical, psychiatric, and neurological disorders or conditions. For example, stimulation of the vagus nerve has been proposed as a method for treating various heart conditions, including heart failure. The nerves stimulated and/or sensed may be sympathetic or parasympathetic in character.

In a nerve stimulation and sensing system, one or more electrodes are formed on a lead that are electrically connected to an implanted electronic package, such as a pulse generator. Electrical energy is delivered to the electrodes by conductors that extend from the pulse generator at a proximal end of the lead to the electrodes at a distal end of the lead. For direct stimulation of a nerve, the electrodes may be configured to be secured directly to, wrapped around, or laid next to the nerve.

SUMMARY

Example 1 is a neurostimulation lead including a lead body and a first conductor extending through the lead body. An electrode cuff is secured relative to a distal portion of the lead body. The electrode cuff includes a cuff body, a first tendril extending from a first region of the cuff body, a second tendril extending from a second region of the cuff body and a first electrode disposed on the cuff body and electrically connected to the first conductor.

Example 2 includes Example 1 and specifies that the first tendril extends from the first region of the cuff body at an acute angle and is biased to a curved configuration in which the first tendril curves in a first direction.

Example 3 includes either of Examples 1 and 2 and specifies that the second tendril extends from the second region of the cuff body at an acute angle and is biased to a curved configuration in which the second tendril curves in a second direction opposite the first direction.

Example 4 includes Example 1 and specifies that the first tendril extends substantially perpendicularly from the first region of the cuff body.

Example 5 includes Examples 1 and 4 and specifies that the second tendril extends substantially perpendicularly from the second region of the cuff body.

Example 6 includes Example 5 and specifies that the first tendril and the second tendril both extend in a same direction from the cuff body.

Example 7 includes Example 5 and specifies that the first tendril and the second tendril extend in opposite directions from the cuff body.

Example 8 includes any of Examples 1 through Example 7 and specifies inclusion of a second conductor extending through the lead body and a second electrode disposed on the cuff body and electrically connected to the second conductor.

Example 9 includes any of Examples 1 through Example 8 and specifies inclusion of a first suture molded into and extending through the first tendril and a second suture molded into and extending through the second tendril.

Example 10 includes any of Examples 1 through Example 9 and specifies that the cuff body is configured to extend less than about 360 degrees about the nerve.

Example 11 includes any of Examples 1 through Example 10 and specifies that the first and second tendrils are each configured to extend more than about 360 degrees about the nerve.

Example 12 includes any of Examples 1 through 9 and specifies that the cuff body is configured to be wrapped around the nerve, thereby extending more than about 360 degrees about the nerve.

Example 13 includes any of Examples 1 through 12 and specifies that the first tendril and the second tendril are portions of a unitary tendril, the unitary tendril biased to a wrapping direction that reverses direction near a midpoint of the unitary tendril.

Example 14 is a neurostimulation lead including a lead body, a first conductor extending through the lead body and a second conductor extending through the lead body. A first cuff is secured relative to a distal portion of the lead body. A second cuff is secured relative to a distal portion of the lead body. A first electrode is disposed on the first cuff body and is electrically connected to the first conductor. A second electrode is disposed on the second cuff body and is electrically connected to the second conductor. The first cuff includes a first cuff body, a first tendril extending from the first cuff body and biased to a curved configuration in which the first tendril curves in a first direction. A second tendril extends from the first cuff body and is biased to a curved configuration in which the second tendril curves in a second direction opposite the first direction. The second cuff includes a second cuff body, a third tendril extending from the second cuff body and biased to a curved configuration in which the third tendril curves in a third direction. A fourth tendril extends from the second cuff body and is biased to a curved configuration in which the second tendril curves in a fourth direction opposite the third direction.

Example 15 includes Example 14 and specifies that the first cuff is secured relative to the distal portion of the lead body via a first lead extension. The first lead extension is secured to the lead body and the first cuff is attached to the first lead extension.

Example 16 includes Examples 14 and 15 and specifies that the second cuff is secured relative to the distal portion of the lead body via a second lead extension. The second lead is extension secured to the lead body and the second cuff is attached to the second lead extension.

Example 17 includes any of Examples 14 to 16 and specifies inclusion of a strain relief secured to the distal portion of the lead body.

Example 18 includes Example 14 and specifies that the first direction is the same as the third direction, and the second direction is the same as the fourth direction.

Example 19 is a method of securing a neurostimulation cuff to a surgically exposed nerve. The neurostimulation cuff is disposed proximate the nerve, the neurostimulation cuff including a cuff body and first and second tendrils extending from the cuff body. The neurostimulation cuff is positioned in position on the nerve. The first tendril is secured in position by wrapping the first tendril around the nerve in a rotational direction. The second tendril is secured in position by wrapping the second tendril around the nerve in the same rotational direction.

Example 20 includes Example 19 and specifies that the first tendril is biased to extend from the cuff body in a first rotational direction and the second tendril is biased to extend from the cuff in a second rotational direction opposite the first rotational direction in order to permit securement of the first and second tendrils by wrapping the first and second tendrils in the same rotational direction.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2 is a schematic illustration of a portion of a neurostimulation lead in accordance with embodiments of the invention.

FIG. 3 is a schematic illustration of a portion of a neurostimulation lead in accordance with embodiments of the invention.

FIG. 4 is a schematic illustration of a cuff suitable for use with the neurostimulation leads of FIGS. 1 to 3.

FIG. 5 is a schematic illustration of a cuff suitable for use with the neurostimulation leads of FIGS. 1 to 3.

FIG. 6 is a schematic illustration of a cuff suitable for use with the neurostimulation leads of FIGS. 1 to 3.

FIGS. 6A and 6B are cross-sectional views of a portion of the cuff shown in FIG. 6.

FIG. 12 is a schematic illustration of a portion of a neurostimulation lead in accordance with embodiments of the invention.

Figure 1A:
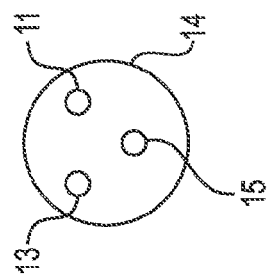
FIG. 1A is a cross-sectional view of the neurostimulation lead shown in FIG. 1.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
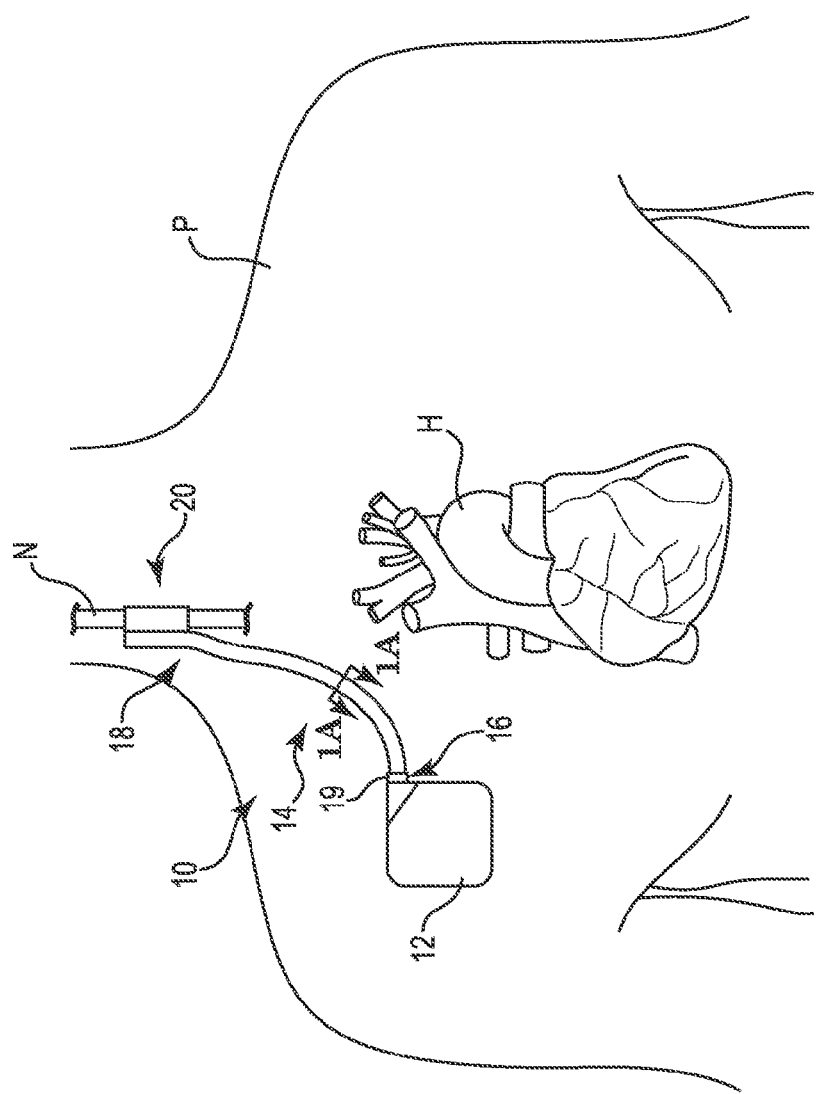
FIG. 1 shows an embodiment of a neurostimulation system according to the present invention and portions of an environment in which the neurostimulation system is used.

FIG. 1 shows an embodiment of a neurostimulation system 10 according to the present invention implanted in a patient P. The neurostimulation system 10 includes an implantable medical device (IMD) 12 with a lead 14 having a proximal end 16 and a distal end 18. In one embodiment, the IMD 12 includes a pulse generator. The IMD 12 can be implanted subcutaneously within the body, typically at a location such as in a patient's chest or abdomen, although other implantation locations are possible. The proximal end 16 of the lead 14 can be coupled to the IMD 12 via one or more connectors 19. Alternatively, the lead 14 may be formed integrally with the IMD 12. The distal end 18 of the lead 14, in turn, can be implanted at a desired location in the patient's body to stimulate excitable tissue.

The distal end 18 of the lead 14 includes one or more electrode cuffs 20. While a single electrode cuff 20 is shown in FIG. 1, it will be appreciated that in some embodiments the lead 14 may include one, two, three or more electrode cuffs 20. Further details regarding the construction and implantation of the electrode cuffs 20 will be described with respect to subsequent FIGS. In some embodiments, a single electrode cuff 20 may include two electrodes (not shown in FIG. 1). In some embodiments, the lead 14 may include several electrode cuffs 20, each with a single electrode. One electrode may, for example, function as a cathode electrode while another electrode may function as an anode electrode. The electrode(s) is(are) electrically connected to the IMD 12 via one or more conductors 11, 13, 15 (shown in FIG. 1A) extending through the lead 14.

During operation, the lead 14 delivers electrical signals between the IMD 12 and the electrode cuffs 20. The electrode cuffs 20 may be separately controlled by IMD 12, such that energy having different magnitude, phase, and/or timing characteristics may be delivered to or from each of the electrode cuffs 20. In some embodiments, one or more of the electrode cuffs 20 can alternatively be configured as a strain relief cuff that does not carry electrical signals, but secures the distal end 18 relative to the nerve N to minimize movement of the electrode cuffs 20 relative to the excitable tissue due to voluntary or involuntary movements of the patient. Furthermore, the IMD 12 shown is merely by way of illustration, and the IMD 12 may have any configuration suitable for use in conjunction with the lead 14 and may be implanted in any suitable location in the patient's body.

The electrode cuffs 20 include electrodes that are configured for stimulation or sensing of a nerve or nerve bundle. In the embodiment shown, the distal end 18 is secured to the vagus nerve N. The electrode cuffs 20 may be arranged around the nerve, with the IMD 12 configured to deliver energy to the electrode cuffs 20 to stimulate the nerve. Stimulating the sympathetic and parasympathetic nervous systems can have effects on physiological parameters associated with the heart H, such as heart rate and blood pressure. In addition, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

The vagus nerve N has afferent properties, such that the neural stimulation is transmitted to the central nervous system (CNS). Vagal stimulation simultaneously increases parasympathetic and decreases sympathetic activity, and is believed to prevent further remodeling or predisposition to fatal arrhythmias in post-myocardial infarction (MI) patients, to help restore autonomic balance and increase heart rate variability (HRV), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development or worsening of congestive heart failure (CHF) following MI. The electrode cuffs 20 may be configured and arranged to stimulate the vagus nerve N to provide any of the physiological responses described. While the electrode cuffs 20 are shown arranged around the right vagus nerve N in FIG. 1, the electrode cuffs 20 can be configured and arranged to stimulate the left vagus nerve to treat other physiological and psychological conditions, such as epilepsy and depression.

FIG. 2 provides a side view of a portion of the lead 14 that includes a lead body 30 and three (as illustrated) electrode cuffs 20. In some embodiments, the lead 14 also includes one or more of a first lead extension 32 and a second lead extension 34. The first and second lead extensions 32, 34 can, if included, each include electrical conductors that provide electrical connections between the IMD 12 and one or more of the electrode cuffs 20. In some embodiments, the electrode cuffs 20 include a strain relief 36, a first electrode cuff 38 and a second electrode cuff 40. In some embodiments, the strain relief 36 is secured to the lead body 30 in order to help mitigate movement of the first and second electrode cuffs 38, 40. The first electrode cuff 38 can be secured to the first lead extension 32 while the second electrode cuff 40 can be secured to the second lead extension 34. In some embodiments, as illustrated, the strain relief 36 can be secured to the lead body 30 by a connector 48. In some embodiments, the connector 48 can also secure at least one of the first lead extension 32 and/or the second lead extension 34, if present, to the lead body 30.

FIG. 3 is similar to FIG. 2 but shows a portion of a lead 14 having a strain relief 42 that is configured as a helical winding that is biased to a coiled configuration as shown. In some embodiments, the strain relief 42 includes a first end 44 and a second end 46, and the strain relief 42 can be wrapped around the nerve N by pulling each of the first end 44 and the second end 46 and wrapping each of the first end 44 and the second end 46 around the nerve N. In some embodiments, as illustrated, the strain relief 42 can be secured to the lead body 30 by a connector 48. In some embodiments, the connector 48 can also secure at least one of the first lead extension 32 and/or the second lead extension 34, if present, to the lead body 30.

FIGS. 4 and 5 provide an illustration of an electrode cuff 50 and an exemplary method of securing the electrode cuff 50 to the nerve N. The electrode cuff 50 is an example of an electrode cuff 20 that can be used in combination with the lead 14. In the illustrated embodiment, the electrode cuff 50 has a first region 52 and a second region 54. A first tendril 56 extends from the first region 52 of the electrode cuff 50 and a second tendril 58 extends from the second region 54 of the electrode cuff 50. In some embodiments, the first tendril 56 and the second tendril 58 curve in opposite directions (with respect to an observer viewing the Figure).

To secure the electrode cuff 50 to the nerve N, the electrode cuff 50 is disposed proximate the nerve N. The electrode cuff 50 can be rotated in a direction indicated by an arrow 60, thereby bringing the first tendril 56 and the second tendril 58 into contact with the nerve N. In some embodiments, the first tendril 56 and the second tendril 58 are sufficiently stiff to permit adequate securement of the electrode cuff 50 to the nerve N without requiring that either of the first tendril 56 or the second tendril 58 extend much beyond a half circle. In some embodiments, the first tendril 56 and/or the second tendril 58 may be sufficiently flexible to permit uncoiling and recoiling the first tendril 56 and/or the second tendril 58 around the nerve N.

FIG. 6 is a schematic illustration of an electrode cuff 70 disposed about the nerve N. The electrode cuff 70 is an example of an electrode cuff 20 that can be used in combination with the lead 14. The electrode cuff 70 includes a cuff body 72 and an electrode 74 that is disposed on or otherwise secured to the cuff body 72. In some embodiments, the electrode 74 may be a foil electrode. While a single electrode 74 is shown, in some embodiments the cuff body 72 may include two or more electrodes 74.

The cuff body 72 includes a first region 76 and a second region 78. A first tendril 80 extends from the first region 76 of the cuff body 72 and a second tendril 82 extends from the second region 78 of the cuff body 72. In some embodiments, the first tendril 80 is biased to a curved configuration as shown. In some embodiments, the second tendril 82 is biased to a curved configuration as shown. In some embodiments, as illustrated, the first tendril 80 extends at an acute angle with respect to the cuff body 72 and the second tendril 82 extends at an acute angle with respect to the cuff body 72. For illustrative purposes, this acute angle is indicated as angle alpha ($\alpha$), which can be in a range greater than zero degrees and less than 90 degrees.

The first tendril 80, the second tendril 82 and the cuff body 72 can be formed of any suitable material. In some embodiments, the first tendril 80, the second tendril 82 and the cuff body 72 are each formed of a polymeric material such as silicone. FIGS. 6A and 6B are cross-sectional views of the first tendril 80 and the second tendril 82, respectively.

In some embodiments, as illustrated, the first tendril 80 can include a first suture 86 that is molded within the first tendril 80 and that extends through the first tendril 80. In some embodiments, as illustrated, the second tendril 82 can include a second suture 88 that is molded within the second tendril 82 and that extends through the second tendril 82. The first suture 86 and the second suture 88 can, if present, aid in deployment of the electrode cuff 70 by providing the surgeon with something that can be grasped and pulled on in order to appropriately wrap the first tendril 80 and/or the second tendril 82 around the nerve N. In some embodiments, as illustrated, the first suture 86 can extend out of the end of the first tendril 80 so that the surgeon can grasp it. In some embodiments, as illustrated, the second suture 86 can extend out of the end of the second tendril 82 so that the surgeon can grasp it.

Figure 7:
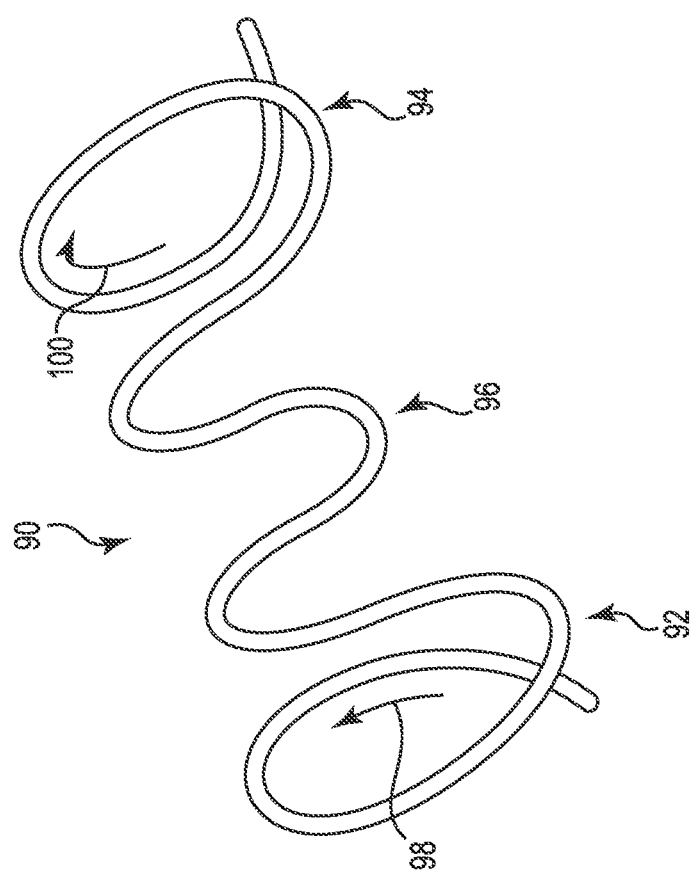
FIG. 7 is a schematic illustration of a cuff suitable for use with the neurostimulation leads of FIGS. 1 to 3.

FIG. 7 is an illustration of a unitary tendril 90 that can form part of the electrode cuffs 20 described herein. The unitary tendril 90 includes a first portion 92 and a second portion 94. The unitary tendril 90 also includes a midpoint 96 where the unitary tendril 90 switches wrapping direction. In some embodiments, as illustrated, the first portion 92 of the unitary tendril 90 can be considered as having a first coil direction indicated by arrow 98 while the second portion 94 of the unitary tendril 90 can be considered as having a second coil direction indicated by arrow 100.

By having either end biased to opposite coil directions, it will be appreciated that the surgeon installing an electrode cuff with such a unitary tendril 90 can wrap or unwrap either end in the same direction, i.e., both ends can be wrapped or unwrapped in a clockwise direction or in a counter-clockwise direction by virtue of the two ends of the unitary tendril 90 extending from opposite ends of the electrode cuff 20. In some situations, this can simplify and speed up the deployment of the electrode cuff 20.

Figure 8:
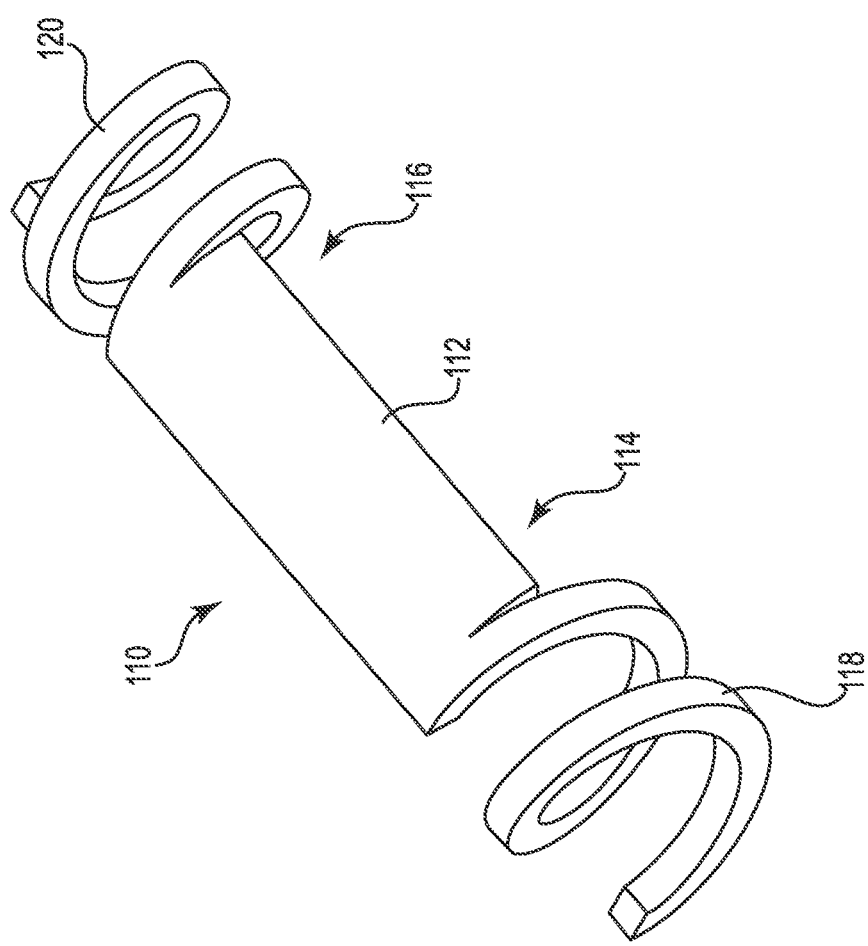
FIG. 8 is a schematic illustration of a unitary tendril suitable for use with the neurostimulation leads of FIGS. 1 to 3.

FIG. 8 illustrates an electrode cuff 110. The electrode cuff 110 is an example of an electrode cuff 20 that can be used in combination with the lead 14. The electrode cuff 110 includes a cuff body 112 and one or more electrodes (not shown). The cuff body 112 includes a first region 114 and a second region 116. A first tendril 118 extends from the first region 114 of the cuff body 112 and a second tendril 120 extends from the second region 116 of the cuff body 112. In some embodiments, the first tendril 118 is biased to a curved configuration as shown. In some embodiments, the second tendril 120 is biased to a curved configuration as shown. While in some respects the electrode cuff 110 is similar to the electrode cuff 70 (FIG. 6), in this instance the first tendril 118 and the second tendril 120 are long enough to wrap several times around the nerve N. In some embodiments, the first tendril 118 and the second tendril 120 are biased to a coiled configuration in which the first and second tendrils 118, 120 have an overall diameter that is greater than a diameter of the cuff body 112.

Figure 9:
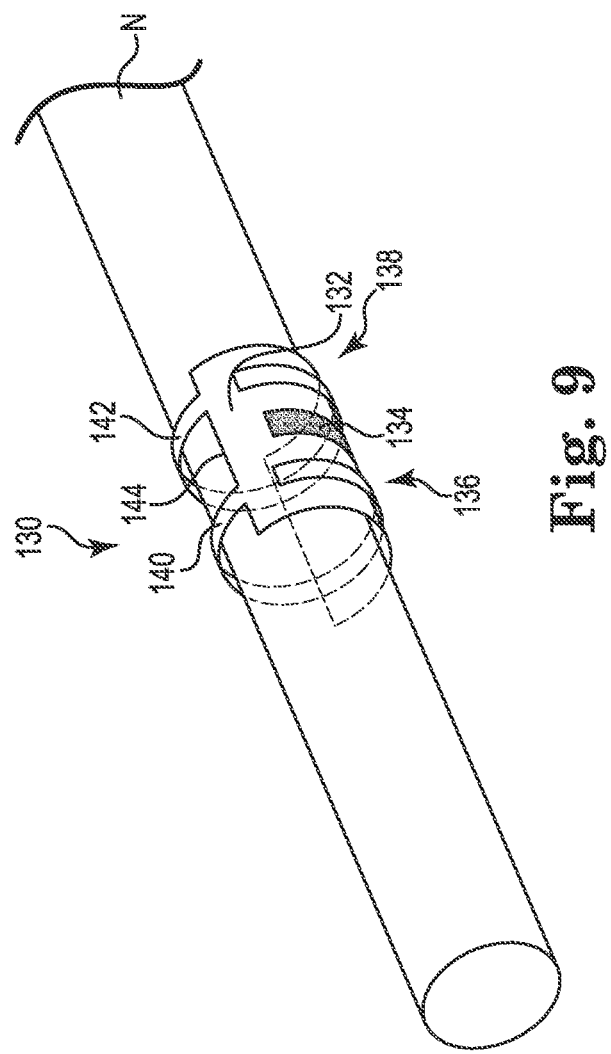
FIG. 9 is a schematic illustration of a cuff suitable for use with the neurostimulation leads of FIGS. 1 to 3.
Figure 10:
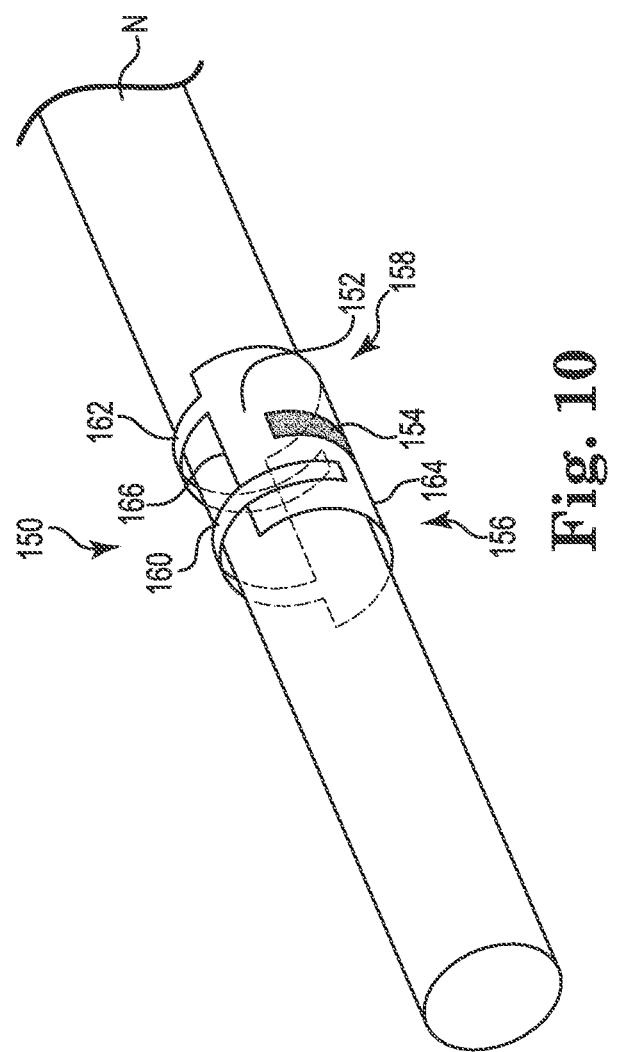
FIG. 10 is a schematic illustration of a cuff suitable for use with the neurostimulation leads of FIGS. 1 to 3.

FIGS. 9 and 10 provide illustrations of electrode cuffs that are configured to minimize the overall length of the electrode cuff and thus minimize the overall cut-down length required for deployment of the electrode cuff. FIG. 9 illustrates an electrode cuff 130 deployed on the nerve N. The electrode cuff 130 is an example of an electrode cuff 20 that can be used in combination with the lead 14. The electrode cuff 130 includes a cuff body 132 and an electrode 134. The cuff body 132 includes a first region 136 and a second region 138. A first tendril 140 extends from the first region 136 of the cuff body 132 and a second tendril 142 extends from the second region 138 of the cuff body 132.

In the illustrated embodiment, the first tendril 140 extends perpendicularly or at least substantially perpendicular to the cuff body 132. The second tendril 142 extends perpendicularly or at least substantially perpendicularly to the cuff body 132. In some embodiments, the first tendril 140 and/or the second tendril 142 extend more than 360 degrees around the nerve N and thus overlap on the cuff body 132. In some embodiments, the first tendril 140 and/or the second tendril 142 may extend less than 360 degrees around the nerve N. The first tendril 140 and the second tendril 142 extend from a common side 144 of the cuff body 132.

FIG. 10 illustrates an electrode cuff 150 deployed on the nerve N. The electrode cuff 150 is an example of an electrode cuff 20 that can be used in combination with the lead 14. The electrode cuff 150 includes a cuff body 152 and an electrode 154. The cuff body 152 includes a first region 156 and a second region 158. A first tendril 160 extends from the first region 156 of the cuff body 152 and a second tendril 162 extends from the second region 158 of the cuff body 152.

In the illustrated embodiment, the first tendril 160 extends perpendicularly or at least substantially perpendicular to the cuff body 152. The second tendril 162 extends perpendicularly or at least substantially perpendicularly to the cuff body 152. In some embodiments, the first tendril 160 and/or the second tendril 162 extend more than 360 degrees around the nerve N and thus overlap on the cuff body 152. In some embodiments, the first tendril 160 and/or the second tendril 162 may extend less than 360 degrees around the nerve N. In the illustrated embodiment, the first tendril 160 extends from a first side 164 of the cuff body 152 and the second tendril 162 extends from a second side 166 of the cuff body 152.

As noted, each of the electrode cuffs described herein, such as the electrode cuff 50, the electrode cuff 70, the electrode cuff 110, the electrode cuff 130 or the electrode cuff 150 can be used in combination with the lead 14 as one or more of the electrode cuffs 20. Each of the electrode cuffs described herein can be formed of any suitable material including a polymeric material such as silicone. In some embodiments, the tendrils can be biased to a particular curved or coiled configuration. In some embodiments, the tendrils can be formed of a shape memory material such as a shape memory polymer.

Figure 11:
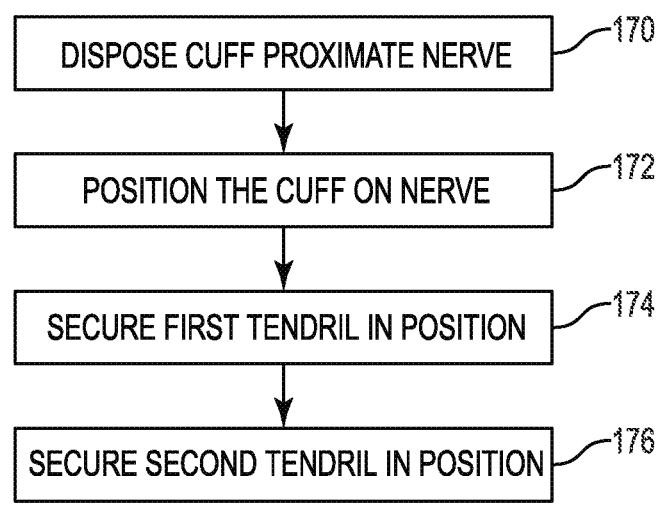
FIG. 11 is a flow diagram illustrating a method that may be carried out using the neurostimulation leads of FIGS. 1 to 3.

FIG. 11 illustrates a method that can be carried out using the lead 14 and the electrode cuffs described herein. An electrode cuff having a first tendril and a second tendril can be disposed proximate the nerve N as generally indicated at block 170. At block 172, the electrode cuff can be positioned on the nerve N. The first tendril can be secured in position on the nerve N as generally indicated at block 174. In some embodiments, the first tendril can be secured by wrapping the first tendril around the nerve in a rotational direction. The second tendril can be secured in position on the nerve N as generally indicated at block 176. In some embodiments, the second tendril can be secured by wrapping the second tendril around the nerve N in the same rotational direction.

FIG. 12 illustrates a lead 214 that includes a first electrode cuff 220 secured to a lead body extension 221 and a second electrode cuff 222 secured to a lead body extension 223. The first electrode cuff 220 includes a first cuff body 224 and a first tendril 226 extending from the first cuff body 224. The first tendril 226 is biased to a curved configuration in which the first tendril 226 curves in a first direction 228. A second tendril 230 extends from the first cuff body 224 and is biased to a curved configuration in which the second tendril 230 curves in a second direction 232.

The second electrode cuff 222 includes a second cuff body 234 and a third tendril 236 extending from the second cuff body 234. The third tendril 236 is biased to a curved configuration in which the third tendril 226 curves in a third direction 238. A fourth tendril 240 extends from the second cuff body 234 and is biased to a curved configuration in which the fourth tendril 240 curves in a fourth direction 242. In some embodiments, the first direction 228 and the third direction 238 can be the same. In some embodiments, the second direction 230 and the fourth direction 240 can be the same.

By having opposing ends of each electrode cuff 220 and 222 biased to opposite coil directions, it will be appreciated that the surgeon installing the electrode cuffs can wrap or unwrap either end in the same direction, i.e., both ends of each electrode cuff 230, 232 can be wrapped or unwrapped in a clockwise direction or in a counter-clockwise direction. In some situations, this can simplify and speed up the deployment.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A neurostimulation lead comprising:
   a lead body having a proximal portion and a distal portion;
   a first conductor extending through the lead body; and
   an electrode cuff secured relative to the distal portion of the lead body, the electrode cuff including:
      a cuff body having a first region and a second region;
      a first tendril extending substantially perpendicularly from an edge of the first region of the cuff body;
      a second tendril extending substantially perpendicularly from an edge of the second region of the cuff body; and
      a first electrode disposed on the cuff body and electrically connected to the first conductor,
      wherein at least one of the first tendril and the second tendril is configured to overlap the cuff body.

2. The neurostimulation lead of claim 1, wherein the first tendril and the second tendril both extend in a same direction from the cuff body.

3. The neurostimulation lead of claim 1, wherein the first tendril and the second tendril extend in opposite directions from the cuff body.

4. The neurostimulation lead of claim 1, further comprising:
   a second conductor extending through the lead body; and
   a second electrode disposed on the cuff body and electrically connected to the second conductor.

5. The neurostimulation lead of claim 1, further comprising:
   a first suture molded into and extending through the first tendril; and
   a second suture molded into and extending through the second tendril.

6. The neurostimulation lead of claim 1, further comprising a strain relief secured to the distal portion of the lead body.

7. The neurostimulation lead of claim 1, wherein the cuff body is configured to extend less than about 360 degrees about the nerve.

8. The neurostimulation lead of claim 1, wherein the first and second tendrils are each configured to extend more than about 360 degrees about the nerve.

9. The neurostimulation lead of claim 1, wherein the electrode cuff is formed of silicone.

10. The neurostimulation lead of claim 1, wherein the first tendril and the second tendril are formed of a shape memory polymer.

11. A neurostimulation lead comprising:
    a lead body having a proximal portion and a distal portion;
    a first conductor extending through the lead body;
    a second conductor extending through the lead body; and
    a first cuff secured relative to the distal portion of the lead body, the first cuff including:
       a first cuff body;
       a first tendril extending substantially perpendicularly from an edge of the first cuff body and configured to overlap the first cuff body;
       a second tendril extending substantially perpendicularly from an edge of the first cuff body and configured to overlap the first cuff body; and
       a first electrode disposed on the first cuff body and electrically connected to the first conductor; and
    a second cuff secured relative to the distal portion of the lead body, the second cuff including:
       a second cuff body;
       a third tendril extending substantially perpendicularly from an edge of the second cuff body and configured to overlap the second cuff body;
       a fourth tendril extending substantially perpendicularly from an edge of the second cuff body and configured to overlap the second cuff body; and
       a second electrode disposed on the second cuff body and electrically connected to the second conductor.

12. The neurostimulation lead of claim 11, wherein the first cuff is secured relative to the distal portion of the lead body via a first lead extension, the first lead extension secured to the lead body and the first cuff being attached to the first lead extension.

13. The neurostimulation lead of claim 12, wherein the second cuff is secured relative to the distal portion of the lead body via a second lead extension, the second lead extension secured to the lead body and the second cuff being attached to the second lead extension.

14. The neurostimulation lead of claim 11, further comprising a strain relief secured to the distal portion of the lead body.

15. The neurostimulation lead of claim 11, wherein the first tendril, the second tendril, the third tendril, and the fourth tendril are each biased to a curved configuration.

16. The neurostimulation lead of claim 11, wherein the first tendril and the second tendril both extend in a first direction from the cuff body, and the third tendril and the fourth tendril extend in a second direction from the cuff body.

17. The neurostimulation lead of claim 16, wherein the first direction and the second direction are the same direction.

18. The neurostimulation lead of claim 16, wherein the first direction and the second direction are opposite directions.

19. The neurostimulation lead of claim 11, wherein the first tendril and the third tendril both extend in a first direction from the cuff body, the second tendril and the fourth tendril both extend in a second direction from the cuff body, and the first direction and the second direction are opposite directions.

20. The neurostimulation lead of claim 11, wherein the first tendril, the second tendril, the third tendril, and the fourth tendril are formed of a shape memory polymer.

* * * * *